United States Patent [19]

Mesa

[11] Patent Number: 5,254,128
[45] Date of Patent: Oct. 19, 1993

[54] SURGICAL KNIFE WITH ATTACHED, MOVABLE BLADE PROTECTOR

[75] Inventor: Bernard E. Mesa, Huntsville, Tex.

[73] Assignee: Micro Engineering, Inc., Huntsville, Tex.

[21] Appl. No.: 595,969

[22] Filed: Oct. 11, 1990

[51] Int. Cl.5 .............................. A61B 17/32
[52] U.S. Cl. ........................ 606/167; 30/151
[58] Field of Search ........... 606/166, 167, 170; 30/151, 156, 162, 163, 286

[56] References Cited

U.S. PATENT DOCUMENTS

| | | |
|---|---|---|
| 2,390,309 | 12/1945 | Keys ....................... 30/151 |
| 3,608,195 | 9/1971 | Levin ...................... 30/162 |
| 3,706,106 | 12/1972 | Leopoldi . |
| 3,905,101 | 9/1975 | Shepherd . |
| 3,915,169 | 10/1975 | McGuire . |
| 3,945,117 | 3/1976 | Beaver . |
| 4,006,746 | 2/1977 | Edwards . |
| 4,026,295 | 5/1977 | Lieberman . |
| 4,074,431 | 2/1978 | Beaver et al. . |
| 4,324,044 | 4/1982 | Shahinian . |
| 4,414,974 | 11/1983 | Dotson et al. . |
| 4,459,059 | 7/1984 | Greenspan . |
| 4,473,076 | 9/1984 | Williams et al. . |
| 4,499,898 | 2/1985 | Knepshield et al. . |
| 4,538,356 | 9/1985 | Knepshield et al. . |
| 4,576,164 | 3/1986 | Richeson .................. 606/167 |
| 4,630,378 | 12/1986 | Kulp et al. . |
| 4,735,202 | 4/1988 | Williams .................. 606/167 |
| 4,736,842 | 4/1988 | Uetake et al. . |
| 4,768,509 | 9/1988 | Grosvenor et al. . |
| 4,790,312 | 12/1988 | Capuano et al. . |
| 4,896,983 | 1/1990 | Im et al. .................... 401/107 |

Primary Examiner—C. Fred Rosenbaum
Assistant Examiner—William W. Lewis
Attorney, Agent, or Firm—Baker & Botts

[57] ABSTRACT

A surgical knife having a body with a blade at one end is provided that has an attached, movable shield that can be moved between either one of two locked positions. The shield can be placed in one position in which it covers and protects the blade and in a second position where it forms a portion of the body for use of the knife.

4 Claims, 2 Drawing Sheets

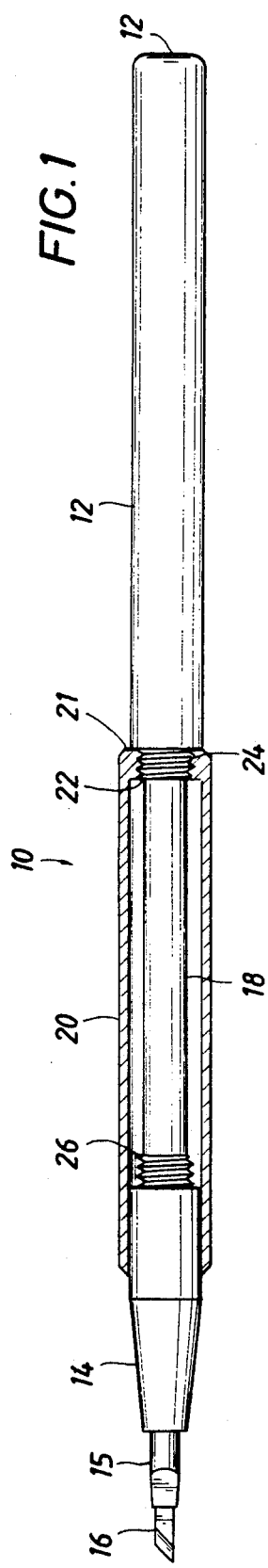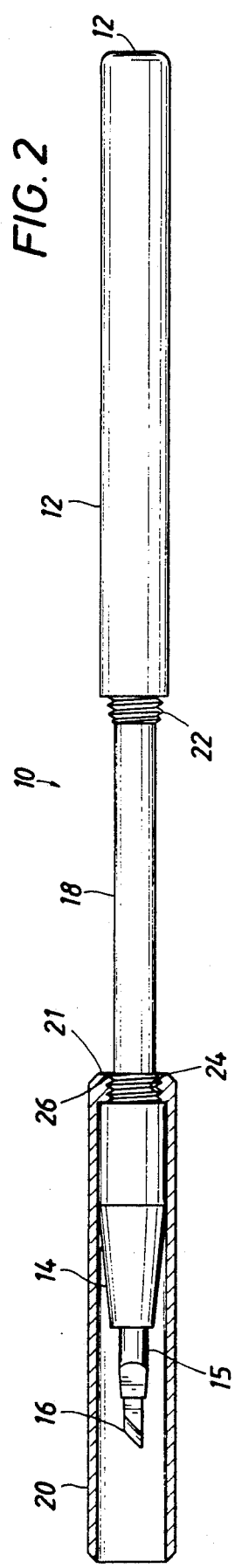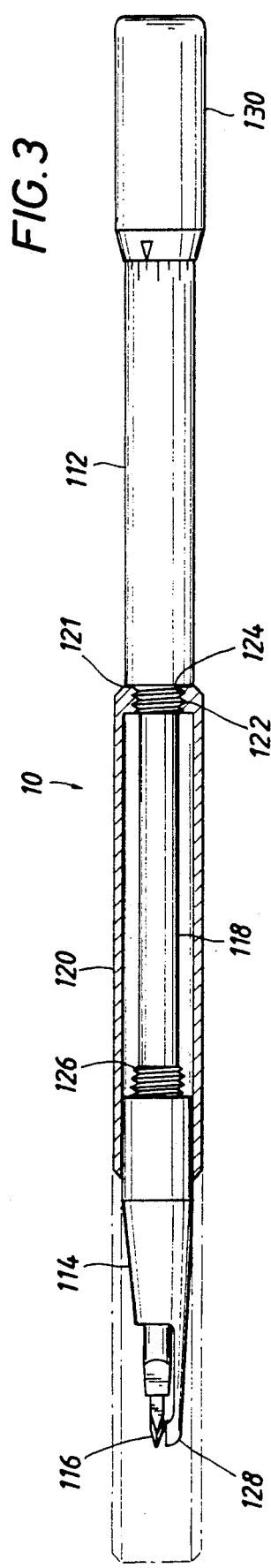

SURGICAL KNIFE WITH ATTACHED, MOVABLE BLADE PROTECTOR

BACKGROUND OF THE INVENTION

This invention relates to surgical knives, and more particularly relates to a surgical knife having an attached, movable blade guard for protecting the knife blade.

One type of surgical knife that has been used in the past has a knife body with a cutting blade at one end of the body. The end of the body with the knife blade also has a portion that tapers down towards the knife blade to provide good visibility of the cutting tip. The blade is extremely sharp, and the extreme sharpness of the blades renders them hazardous when these knives are being passed back and forth during use in surgical operations. If the knife has already been used on the patient, then there is a potential danger of infection since the sharp knife can very easily cut a glove and the skin beneath the glove. Also, the actual cutting edges of these knives are very easy to damage, so that if a knife edge contacts another surgical instrument or an instrument tray or any other hard substance the blade can be damaged or ruined completely.

Accordingly, it seems desirable to provide a way to protect the integrity of the edge on the cutting blade. Such a protective structure should be economical and simple to manufacture, with a minimum amount of effort required to position the structure to protect the blade.

U.S. Pat. No. 4,576,164 to Richeson teaches a disposable micro surgical knife having a shroud that can be locked into a position protecting the blade. The shroud is in the form of a cylindrical sheath that moves axially along and around the knife body. In addition, the shroud has a plurality of projections which mate with a series of longitudinal and circumferential grooves formed in the exterior of the knife body. This arrangement of grooves on the knife body and projections on the shroud allow the shroud to be locked in two or three different axial positions on the knife body. In one position the shroud acts as an enlarged handle, and in a different position the shroud acts as a protective device for the blade and blade edges. However, if the shroud is damaged or slips off and is lost, then the knife body has undesirable grooves on its outer surface that may "feel" so different to a surgeon that it may prevent its use.

U.S. Pat. No. 4,414,974 to Dodson, et al. discloses a surgical knife with a shroud similar to the one disclosed by Richeson. However, this patent does not have a shroud with projections, and it does not have the longitudinal or circumferential grooves on the exterior surface of the knife body. Instead, this patent relies upon friction between some oversized portions of the body and the opening in the shroud for a frictional fit; in one axial position the shroud is retracted for use and in another axial position is in a blade protective position. However, this shroud may slip from its desired position if the frictional fit is inadequate, which may result from normal use and wear and tear.

U.S. Pat. No. 4,735,202 to Williams also teaches a disposable micro surgical knife having a blade guard. The blade guard is basically a cylindrical sleeve that has a longitudinal slot that extends to one end of the sleeve. The knife body has a small locking tab adjacent the forward tapered portion of the knife. The blade guard slides onto the knife body from the rear until the locking tab enters the longitudinal slot and the guard is rotated to be locked into place. Thus, the blade guard can be locked into a blade covering position and then totally removed from the knife body for use of the knife. However, this blade guard may be easily damaged or lost after removal, thereby defeating its purpose.

In a similar manner, U.S. Pat. No. 4,768,509 to Grosvenor et al. discloses a removable external blade guard. U.S. Pat. Nos. 3,706,106; 3,905,101; and 3,945,117 disclose other types of surgical knives having movable or removable blade protective structures. These knives suffer from the same or similar limitations as described hereinbefore.

These and other limitations and disadvantages of the prior art are overcome by the present invention, however, and an improved surgical knife with an improved attached, movable blade protector is provided for preventing damage to the knife blade of a surgical knife when it is not in use.

SUMMARY OF THE INVENTION

In a preferred embodiment of the present invention, a surgical knife with an attached, movable blade protector, is provided. The blade guard is in the form of a cylindrical sleeve with an end portion that may be moved axially along a reduced diameter portion of the knife body. The reduced portion of the body of the knife and the end portion of the sleeve preferably have threads to allow the sleeve to be rotated and threadedly locked into either one of two positions; in a first position, the sleeve substantially entirely surrounds and protects the cutting blade and is in a fixedly spaced relation to the blade. The sleeve may also be rotated to be unscrewed and then slipped back from the knife blade and rotated to threadedly engage a second set of threads on the reduced portion of the knife body to form part of the knife body in a second locked position. That is, the sleeve is movable along a reduced diameter portion of the knife body and may be disposed in a forward position wherein the knife blade is entirely within the confines of the sleeve but spaced therefrom, and the sleeve is further disposable in a rearward position where it covers the reduced diameter portion and forms part of the knife body and the knife blade is exposed for use. Threads are preferably used to ensure that the shroud or sleeve can be positively locked in the blade covering position or in the blade using position; other locking means, such as spring loaded balls and grooves or other spring type devices, may be used.

It is an object of the present invention to provide a surgical knife having an attached, movable blade guard for protecting the blade during sterilization or non-use.

It is another object of the present invention to provide a surgical knife with an attached, moveable blade guard that is easily movable between an operating or use position and protective position.

It is yet a further object to provide a surgical knife with an attached, moveable blade guard that positively locks with the knife body and utilizes a locking structure that does not interfere with the grip on the knife body.

These and other objects and advantages of the present invention will become apparent from the following detailed description, wherein reference is made to the figures in the accompanying drawings.

IN THE DRAWINGS

FIG. 1 is a simplified pictorial illustration of a side view of a surgical knife with a cross-sectional view of the attached, movable blade protector of the present invention positioned in a blade use position.

FIG. 2 is simplified pictorial illustration of a side view of a surgical knife with a cross-sectional view of the attached, movable blade protector of the present invention positioned in a blade protective position.

FIG. 3 is a simplified pictorial illustration of a side view of a different surgical knife with a cross-sectional view of the attached, movable blade protector of the present invention positioned in a blade use position and a dashed outline representing the blade protector in the blade protective position.

DETAILED DESCRIPTION

Figure 4:
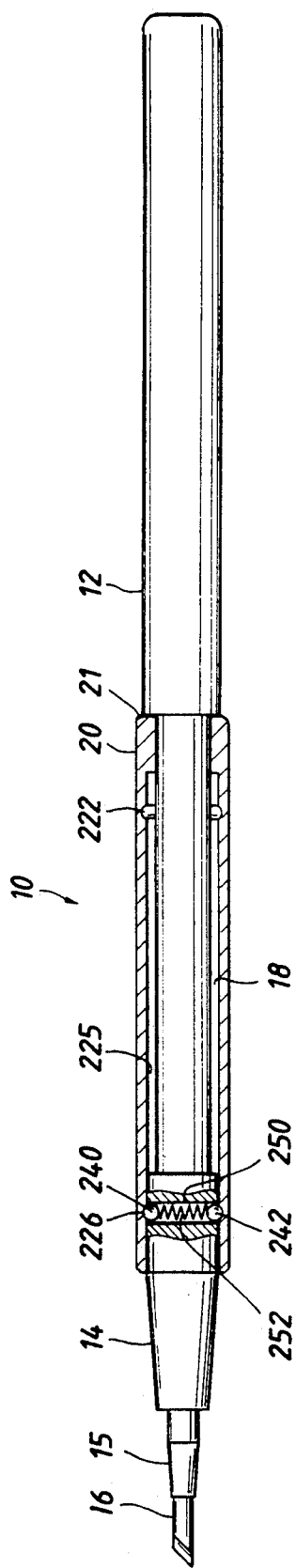
FIG. 4 is a simplified pictorial illustration of a side view of a different surgical knife with a cross-sectional view of the attached, movable blade protector of the present invention in a blade use position.

Referring now to FIG. 1, there may be seen a preferred embodiment of the present invention, depicted as a simplified pictorial illustration of a side view of a surgical knife with a partial cross-sectional view of the attached, movable blade protector of the present invention. It may be seen from FIG. 1 that the surgical knife includes generally a knife body 10 that consists of a rearward, generally cylindrical portion 12 and a forward tip portion 14 that is generally frustoconical in shape. The tip 14 includes an appropriate mounting 15 for a cutting blade 16. Preferably, the blade 16 is a diamond blade that will keep a very sharp edge for a long period of time in order to provide a reusable knife. In particular, it may be seen that forward tip portion 14 tapers downwardly toward the blade 16 to provide good visibility of the cutting edge of the knife.

There may also be seen a reduced diameter portion 18 of the knife body 10 disposed between and interconnected with rearward portion 12 and forward tip 14. Shield 20 is the attached, movable blade protector of the present invention. It may be seen that shield 20 has an end wall portion 21 that is disposed around the reduced diameter portion 18. It may also be seen that the end wall portion 21 includes female threads 24; threads 24 may engage male threads 22 which are at one end of portion 18. Thus, shield 20 may be rotated to engage its threads 24 with threads 22 to lock the shield 20 into place so that the knife may be used in this configuration; other locking means may also be employed. Shield 20 also covers reduced portion 18 in this configuration and forms part of the handle or grip for knife body 10. Further, shield 20 is slidably but snugly fitted around tip 14 to provide a rigid grip for knife body 10, when shield 20 is in the "use" position.

Referring now to FIG. 2, it may be seen that shield 20 has been moved into a blade protective position. More particularly, it may be seen that shield 20 has been moved toward the forward tip 14 of the knife body 10. The shield 20 may be locked into this position by engaging its female threads 24 with a second set of male threads 26 which are at the other end of reduced diameter portion 18 of the knife body 10. Thus, shield 20 may be rotated about its cylindrical axis to engage its threads 24 with threads 26 located on the knife body; other locking means may be employed. Further, shield 20 may be slidably moved along reduced portion 18 between either one of the two positions corresponding to the threads 22 and 26 on the reduced diameter portion 18 of the knife body 10.

Shield 20 is a cylindrical sleeve having an inside diameter that is slightly greater than the corresponding outside diameter of the generally cylindrical portion of the forward tip 14. In this manner shield 20 may be easily slid from the blade use position corresponding to FIG. 1 to the blade protective position corresponding to FIG. 2. As noted herein before, the threads 24 are in an end wall portion 21 at one end of shield 20 and are selectively engageable with the threads 22 and 26 on the reduced diameter portion 18 to lock shield 20 into either one of these two positions. However, other locking means may be employed. Further, the inside diameter of the opening in end wall portion 21, which preferably includes threads 24, is slightly greater than the outside diameter of reduced portion 18.

Figure 5:
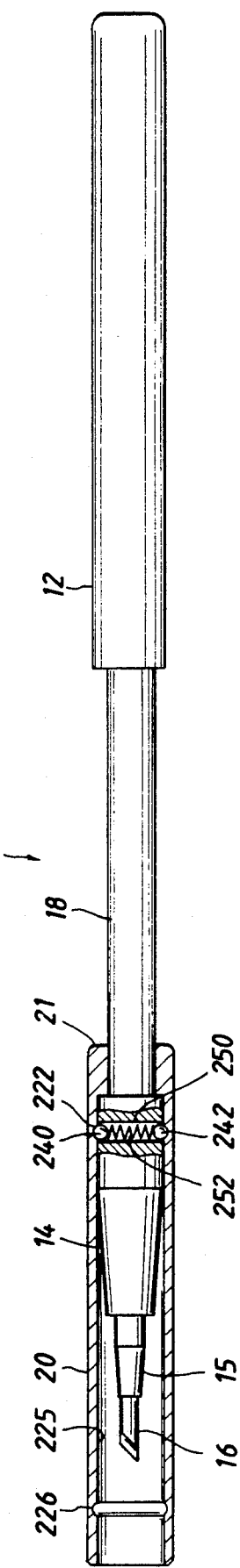
FIG. 5 is a simplified pictorial illustration of a side view of the knife of FIG. 4 with a crosssectional view of the blade protector in a blade protective position.

Although FIGS. 1-3 depict threads as the presently preferred locking means, other locking means may be employed. For example, in FIGS. 4 and 5 the locking means may consist of interior circumferential grooves 222, 226 in the interior wall 225 of shield 20 adjacent both ends of shield 20. Metal balls 240, 242 that are located in and at the ends of an opening 250 along a diameter and through tip 14 may be pushed into engagement with one of these circumferential grooves 222, 226, by a spring 252 disposed between the two balls 240, 242 at the ends of the opening 250 and biasing the two balls outwardly; that is, the opening 250 is a hole from one side of tip 14 to the other side and contains the spring 252 and outwardly biased balls, 240, 242 with one ball on each side of tip 14. This allows the balls 240, 242 to "click" into a groove 222, 226 in shield 20 to lock shield 20 into either one of its two locked positions, while allowing shield 20 to be moved freely from one position to the other. In a similar manner, other types of spring loaded (coiled spring or leaf spring) detents may be employed to "click" into the grooves to lock shield 20 into one of its two positions. For example, a bowed leaf spring attached at both ends to said tip and having a rounded projection on its upper most portion would serve as such a spring loaded detent. In addition, a snap ring arrangement could be used as a detent to "click" into grooves to lock shield 20 into position.

Although the FIGS. 1-2 depict the outside diameter of the generally cylindrical portion of the forward tip 14 as having the same outside diameter as that of the generally cylindrical rearward portion 12 of the knife body 10, clearly the forward tip outside diameter need not be the same as the outside diameter of portion 12. However, in general, the outside diameter of the rearward portion 12 must be larger than the outside diameter of the reduced diameter portion 18, so that the end of cylindrical portion 12 serves as a physical stop against which shield 20 may be screwed to lock it into position. Further, portion 12 need not have the same diameter along its entire length; for some embodiments, portion 12 may preferably have a tapered configuration, with the narrow portion of the taper at the end of the body 10 opposite the blade 16. Similarly, the outside diameter of the generally cylindrical portion of forward tip 14 must be larger than the outside diameter of the reduced diameter portion 18 to serve as a forward physical stop when the shield 20 is in the blade protective position.

In general, the distance between the threads (22 and 26) on portion 18 should be sufficient to allow for the length of shield 20 to cover threads 26 in the use position and allow shield 20 to extend well beyond blade 16 in the protective position. Similarly, the length of shield 20 is selected so as to extend well beyond blade 16 when in the blade protective position and is dependent upon the length of tip 14 and mounting for blade 16, as well as the length of blade 16 when mounted. Once the approximate position of threads 26 (or other locking means) are selected then the length of shield 20 may be determined; then the position of threads 22 (or other locking means), and accordingly the length of reduced diameter portion 18, may be determined.

Depending upon the type of materials used to manufacture the knife body 10, either the cylindrical portion 12 or the forward tip 14 may be mechanically pressed onto or otherwise mechanically affixed (such as by set screws) to the remainder of the knife after the shield 20 is attached to the knife body 10; this allows for assembly of the shield 20 onto the knife body, but prevents removal or loss of shield 20 after assembly. That is, during assembly, the shield 20 may be screwed onto and across threads 26 and then moved along reduced diameter portion 18 and screwed onto threads 22 to allow for insertion of the forward tip 14, or the shield may be screwed onto and across threads 22 and then moved down to threads 26 to allow for attachment of generally cylindrical portion 12 onto the knife body 10.

Preferably, the knife body elements are made of hard, durable and heat resistant materials or metals and the knife blade is diamond. Such metals may be, for example, but not limited to stainless steel, aluminum, or titanium, and such materials may be, for example, but not limited to composites or carbon fiber impregnated resins. These types of metals are resistent to the steam and heat required to sterilize a surgical knife after each use. Preferably, if the knife body is made of solid metal, such as for a dissection knife, the forward tip 14 is detachable to allow for attachment of shield 20 to the knife body. If the knife body is constructed from metal tubing, such as for a surgery knife, then the forward tip 14 and the generally cylindrical portion 12 may both be detachable, and there may be a center portion which is the generally reduced diameter portion 18 having the threads with appropriate extensions beyond the threads (22, 26) to allow for the addition of generally cylindrical portion 12 and forward tip 14. When tubing is used, the tip 14 can be a solid "plug" of material which is inserted into the interior of the tubing, and the generally cylindrical portion 12 may be tubing which is press-fit (or otherwise secured) onto the extension of the tubing from reduced diameter portion 18 extending beyond threads 22.

Thus, it may be seen that shield 20 stays on the knife body and forms an integral portion of the knife body during use of the cutting blade. That is, the shield is unitary with and becomes part of the knife body. However, the shield is also movable axially along the knife body to either one of two locked positions. In addition, locking means, such as the threads 22 and 26 on the reduced diameter portion 18 of the knife allow for the engagement of threads 24 at one end of the shield, ensure that shield 20 is locked into either one of these two positions.

Referring now to FIG. 3, there may be seen a different embodiment of a surgical knife that may also employ the features of the shield of the present invention. More particularly, there is shown a surgical knife 100 with a generally cylindrical portion 112 and a forward tip 114 of generally frustoconical shape. The cutting blade 116 is located at the forward end of the knife, and the shield 120 is disposed around a reduced diameter portion 118. For this embodiment, the locking means are preferably threads 124 in end wall portion 121 associated with shield 120 which may be selectively engageable with threads 122 or 126 which are located at the ends of the reduced diameter portion 118; other locking means may be employed. Further, there may be seen that there is a ski 128 near the cutting blade 116 and a micrometer 130 at the rearward end of the surgical knife; the micrometer may be employed to adjust the position of either the knife or the ski relative to the knife body. For the embodiment depicted in FIG. 3, the micrometer would move the knife blade relative to the fixed ski 128. However, clearly the knife blade may be fixed and the ski member may be moved by micrometer 130.

The shield 120 again slides along reduced diameter portion 118 between the use position (depicted as solid lines in FIG. 3) and a protective position (depicted in an outline form by a "dashed" line in FIG. 3). The shield is rotated about its cylindrical axis to selectively engage threads 122 or 126 and lock the shield 120 in either of its two positions. For this embodiment, the internal portion of the knife body 100 should be mostly hollow to allow for inclusion of the micrometer drive components in the body 100. The assembly of shield 120 onto body 100 may be as described herein before, and as dictated by assembly of the micrometer drive components.

For this embodiment, shield 120 has a further advantage of allowing the blade 116 (or ski 128) to be left at its desired setting (via micrometer 130). That is, shield 120 protects blade 116 (and ski 128) in the blade protective position and does not require the surgeon to retract blade 116 (or extend ski 128) to protect blade 116 during non-use.

Many other variations and modifications may be made in the apparatus hereinbefore described, by those having experience in this technology, without departing from the concept of the present invention. Accordingly, it should be clearly understood that the apparatus depicted in the accompanying drawings and referred to in the foregoing description is illustrative only and is not intended as any limitation on the scope of the invention.

What is claimed is:

1. A reusable surgical knife having an attached, moveable blade protector, comprising:
an elongated knife body having a generally cylindrical portion of reduced and fixed diameter disposed between a generally cylindrical portion and a frustoconical portion,
a cutting blade extending from said frustoconical portion of said knife body,
a shield member having therethrough an opening for receiving said frustoconical portion of said knife body and having an end wall portion with an opening therethrough for receiving said reduced diameter portion of said knife body and wherein said end wall portion is selectively slidable along and around said reduced diameter portion of said knife body, and locking means for engaging a portion of said end wall portion for locking said shield member in either one of two locked positions.

2. The knife as claimed in claim 1, wherein said locking means comprises:
   a first exterior threaded portion adjacent one end of said reduced diameter portion,
   a second exterior threaded portion adjacent the opposite end of said reduced diameter portion,
   and wherein said end wall portion of said shield member has an interior threaded portion therein.

3. A reusable surgical knife having an attached, moveable blade protector, comprising:
   an elongated knife body having a generally cylindrical portion of reduced and fixed diameter disposed between a generally cylindrical portion and a frustoconical portion,
   a cutting blade extending from said frustoconical portion of said knife body,
   a shield member having therethrough an opening for receiving said frustoconical portion of said knife body and having an end wall portion with an opening therethrough for receiving said reduced diameter portion of said knife body and wherein said end wall portion is selectively slidable along and around said reduced diameter portion of said knife body,
   a first interior circumferential groove adjacent a first end of said shield member,
   a second interior circumferential groove adjacent a second end of said shield member, and
   means for selectively engaging one of said interior grooves located on said frustoconical portion of said knife body.

4. A reusable surgical knife having an attached, moveable blade protector, comprising:
   an elongated knife body having a generally cylindrical portion of reduced diameter disposed between a generally cylindrical portion and a frustoconical portion,
   a cutting blade extending from said frustoconical portion of said knife body,
   a shield member having therethrough an opening for receiving said frustoconical portion of said knife body and an end wall portion having an opening therethrough for receiving said reduced portion of said knife body that is selectively slidable along and around said reduced portion of said knife body, and
   locking means for locking said shield member in either one of two locked positions, wherein said locking means comprises a first interior circumferential groove adjacent a first end of said shield member, a second interior circumferential groove adjacent a second end of said shield member, and means for selectively engaging one of said interior grooves located on said frustoconical portion of said knife body, wherein said means for selectively engaging comprises an opening through said frustoconical portion from one side to the opposite side, a pair of balls disposed in said opening with one of said pair adjacent each of said sides, and a biasing means disposed in said opening for pushing said balls outwardly.

* * * * *